(12) United States Patent
Kerby et al.

(10) Patent No.: US 11,666,311 B2
(45) Date of Patent: Jun. 6, 2023

(54) METHOD AND SYSTEM FOR SWITCHING BETWEEN A SPECTRAL DOPPLER MODE AND A TWO-DIMENSIONAL (2D) ULTRASOUND IMAGING MODE IN AN ULTRASOUND IMAGING SYSTEM

(71) Applicant: Clarius Mobile Health Corp., Burnaby (CA)

(72) Inventors: Benjamin Eric Kerby, Richmond (CA); Kris Dickie, Vancouver (CA); Trevor Stephen Hansen, North Vancouver (CA); Laurent Pelissier, North Vancouver (CA); Reza Zahiri, Burnaby (CA)

(73) Assignee: Clarius Mobile Health Corp., Vancouver (CA)

( * ) Notice: Subject to any disclaimer, the term of this patent is extended or adjusted under 35 U.S.C. 154(b) by 637 days.

(21) Appl. No.: 16/521,494

(22) Filed: Jul. 24, 2019

(65) Prior Publication Data
US 2021/0022716 A1 Jan. 28, 2021

(51) Int. Cl.
*A61B 8/08* (2006.01)
*A61B 8/00* (2006.01)
(Continued)

(52) U.S. Cl.
CPC ............ *A61B 8/5246* (2013.01); *A61B 8/465* (2013.01); *A61B 8/469* (2013.01); *A61B 8/488* (2013.01);
(Continued)

(58) Field of Classification Search
CPC ....... A61B 8/5246; A61B 8/465; A61B 8/469; A61B 8/488; A61B 8/0891; A61B 8/463;
(Continued)

(56) References Cited

U.S. PATENT DOCUMENTS

2005/0203401 A1* 9/2005 Takimoto ............... A61B 8/06
600/441
2007/0265531 A1 11/2007 He et al.
(Continued)

OTHER PUBLICATIONS

Moorthy, Brig RS, "Doppler Ultrasound", MJAFI 2002; 58: 01-02, available online: https://www.ncbi.nlm.nih.gov/omc/articles/PMC4923974/, last accessed Jan. 21, 2020.

*Primary Examiner* — Joseph M Santos Rodriguez
*Assistant Examiner* — Kaitlyn E Sebastian
(74) *Attorney, Agent, or Firm* — Julian Ho; Susan Ben-Oliel (57) ABSTRACT

An ultrasound scanner in a spectral Doppler mode, in which a corresponding two-dimensional (2D) ultrasound imaging mode (e.g., B-mode) image is frozen, is switched temporarily to the 2D-mode in response to a continuous contact on a touchscreen. During the continuous contact, the spectral Doppler mode is interrupted, the 2D-mode image becomes live, and the gate for the spectral Doppler mode may be adjusted by a movement of the continuous contact on the touchscreen. Upon termination of the continuous contact, the system reverts back to the spectral Doppler mode, which now operates within the adjusted gate, and the 2D-mode image is frozen. A brief contact may be used to check the position of the gate against a live 2D-mode image without adjusting it.

20 Claims, 5 Drawing Sheets

(51) Int. Cl.
  *G06F 3/0481* (2022.01)
  *G06F 3/0488* (2022.01)
  *G06F 3/0484* (2022.01)
  *G06F 3/04883* (2022.01)
  *G06F 3/04845* (2022.01)
  *G06F 3/04817* (2022.01)

(52) U.S. Cl.
  CPC ...... *G06F 3/04817* (2013.01); *G06F 3/04845* (2013.01); *G06F 3/04883* (2013.01); *G06F 2203/04806* (2013.01); *G06F 2203/04808* (2013.01)

(58) Field of Classification Search
  CPC ... A61B 8/54; G06F 3/04817; G06F 3/04845; G06F 3/04883; G06F 2203/04806; G06F 2203/04808; G06F 3/04847; G06F 3/04842
  See application file for complete search history.

(56) References Cited

U.S. PATENT DOCUMENTS

| | | |
|---|---|---|
| 2014/0276057 A1 | 9/2014 | Lee et al. |
| 2015/0351726 A1 | 12/2015 | Menon et al. |
| 2016/0007965 A1* | 1/2016 | Murphy .............. G06F 3/04845 |
| | | 345/173 |
| 2018/0116633 A1* | 5/2018 | Hansen .................... A61B 8/54 |
| 2019/0049567 A1 | 2/2019 | Martins |
| 2019/0090855 A1* | 3/2019 | Kobayashi ............. A61B 8/463 |

* cited by examiner

METHOD AND SYSTEM FOR SWITCHING BETWEEN A SPECTRAL DOPPLER MODE AND A TWO-DIMENSIONAL (2D) ULTRASOUND IMAGING MODE IN AN ULTRASOUND IMAGING SYSTEM

TECHNICAL FIELD

This disclosure relates generally to obtaining and viewing ultrasound images. In particular, it relates to switching between different modes of an ultrasound scanner.

BACKGROUND

Ultrasound is a useful, non-invasive imaging technique capable of producing real time images. Ultrasound imaging has an advantage over X-ray imaging in that ultrasound imaging does not involve ionizing radiation.

Ultrasound imaging systems may generally be operated in various Doppler modes that take advantage of the fact that reflected echoes undergo a change in frequency when reflected by moving objects in tissue (e.g., blood). Some Doppler modes include: spectral Doppler, pulsed wave (PW) Doppler, continuous wave (CW) Doppler, color Doppler, and Power Doppler. Tissue Doppler Imaging (TDI) is also a particular way of using spectral or Color Doppler for visualizing tissue wall motion using a lower frequency signal acquisition rate. It can be interchanged with the use of PW Doppler and Color Doppler as necessary.

When an ultrasound scanner is used in a PW Doppler mode, it allows the operator to select a specific, small area on the image, and, in the tissue corresponding to that area, measure blood motion velocity. As part of this process, a gate is specified by the user, along an ultrasound beam line or direction (e.g., a one-dimensional signal is obtained). At the gate location, an algorithm is applied to process high-pass filtered, demodulated data into a Fourier transform, in order to look at low-frequency motion of structures, such as blood, within the gate. The result is a spectrum as a function of time that shows the general velocity at the gate location.

In order to obtain a PW Doppler signal, the tissue at the gate location has to be sampled at regular intervals. The frequency with which the ultrasound beam is acquired is called the pulse repetition frequency (PRF). Generally, the higher the PRF, the higher speed blood can be visualized and/or estimated. Since PW Doppler signals do not provide information about the structure of where the echo signal originated, PW Doppler imaging is often combined with a two-dimensional ultrasound imaging mode ("2D-mode") such as B-mode (brightness mode) that provides a 2-D image of the structure being imaged. This is called duplex scanning, where multiple types of ultrasound signals are interleaved to generate a live ultrasound image with multiple types of data together. In particular, B-mode ultrasound signals and PW ultrasound signals can be interleaved together to provide a live 2-D image of structure being imaged and also PW Doppler data where the gate is placed. Duplex scanning is useful for ensuring that the gate location remains accurate while the PW Doppler signal is being acquired. For example, duplex scanning may allow the operator to monitor the B-mode images while obtaining the PW Doppler spectrum to ensure that the gate remains on the tissue desired to be sampled (e.g., that the gate is not moved due to movement of the patient or the transducer).

However, there are certain limitations to operating in duplex scanning. For example, at higher PRF or when the gate is positioned deeper under the skin surface, there may not be enough time between successive PW Doppler samplings to acquire B-mode lines. For instance, at an imaging depth of 10 cm, the B-mode PRP (pulsed repetition period, the inverse of PRF) may be 200 μsec. At a 1 kHz Doppler PRF, the PRP is 1000 μsec, so roughly 4 B-mode lines can fit between a consecutive pair of Doppler lines. If the Doppler PRF becomes 5 kHz, a resulting PRP of 200 μsec would be yielded, making it impossible for B-mode lines to fit in between a consecutive pair of Doppler lines. When B-mode lines cannot be fit because of PRP constraints, there are typically two options: (a) use mono PW mode, where only PW samplings are obtained and the B-mode is turned off but B-mode can be manually toggled on by the operator when desired; or (b) use duplex in an interrupted mode, where a block of PW lines is acquired, then a small pause is introduced to acquire a block of B-mode lines. The interrupted piece of the Doppler signal is then reconstructed using signal analysis in the time domain, which may not necessarily result in a clean Doppler signal. The frame rate of the B-mode image feed may also be significantly impacted in this interrupted duplex mode.

Since the interrupted duplex mode may result in various artifacts on the spectrum, the mono mode may be desirable to be used to obtain the best quality of spectrum. However, in the mono mode, the B-mode images are no longer acquired live, so that if the body or ultrasound scanner moves while scanning, the PW gate may end up in the wrong location. An operator may thus have to toggle between a PW Doppler mode to B-mode imaging to check or adjust the position of the gate and/or the position of the scanner on the body.

In traditional ultrasound systems, the action to switch from PW Doppler mode to B-mode is cumbersome. For example, some traditional ultrasound systems may require a button press for switching between the two modes. After that, while the B-mode is live, and input may be received via a trackball to place the gate in the desired location. The operator may then be required to press a button again to get back to the live PW Doppler mode. This may be inefficient for the operator if they are frequently toggling between the two modes.

There is thus a need for improved ultrasound systems and methods for switching between spectral doppler and a 2-D mode in an ultrasound imaging system. The above background information is provided to reveal information believed by the applicant to be of possible relevance to the present invention. No admission is necessarily intended, nor should be construed, that any of the preceding information constitutes prior art against the present invention. The embodiments discussed herein may address and/or ameliorate one or more of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF DRAWINGS

The following drawings illustrate embodiments of the invention and should not be construed as restricting the scope of the invention in any way.

DETAILED DESCRIPTION

A. Glossary 2D-mode: refers to any ultrasound imaging mode that provides a two-dimensional cross-sectional view of body tissue, and may include B-mode, a combined B-mode/Color Doppler mode, or a combined B-mode/Power Doppler mode.

B-mode: refers to the brightness mode of an ultrasound scanner, which displays the acoustic impedance of a two-dimensional cross-section of body tissue.

Spectral Doppler: a Doppler imaging mode of an ultrasound scanner using a single focused line to sample data at a given region (for example, in a blood vessel to visualize blood velocity).

PW: a pulsed wave Doppler mode, which uses time of flight calculations to obtain signals from a given region, showing direction and speed through a one-dimensional spectrum that is updated over time.

CW: a continuous wave Doppler mode, which continuously transmits and receives at a single region to obtain signals, and can be used for high speed blood flow measurements.

Color or Color Doppler: a color Doppler imaging mode that characterizes blood flow across a 2-dimensional image, showing direction and speed.

Power or Power Doppler: a power Doppler imaging mode that characterizes blood flow across a 2-dimensional image, showing intensity but not direction or speed.

PRF: pulse repetition frequency, the frequency in which an ultrasound beam is acquired.

PRP: pulsed repetition period, the inverse of PRF.

The term "operator" may refer to the person that is operating an ultrasound scanner and/or ultrasound system (e.g., a clinician, medical personnel, a sonographer, ultrasound student, ultrasonographer and/or ultrasound technician).

The term "module" can refer to any component in the embodiments and to any or all of the features of the described embodiments without limitation. A module may be a software, firmware or hardware module, and may be located, for example, in the scanner, the interface, a network, a display device and/or a server.

The term "network" can include a mobile network and/or data network without limiting the term's meaning, and includes the use of wireless (e.g. 2G, 3G, 4G, 5G, Wi-Fi™, WiMAX™, Wireless USB (Universal Serial Bus), Zigbee™, Bluetooth™ and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A network could also mean dedicated connections between computing devices and electronic components, such as buses for intra-chip communications.

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by code or a module. The processor, if comprised of multiple processors, may be located together or geographically separate from each other. The term includes virtual processors and machine instances as in cloud computing or local virtualization, which are ultimately grounded in physical processors.

Figure 3:
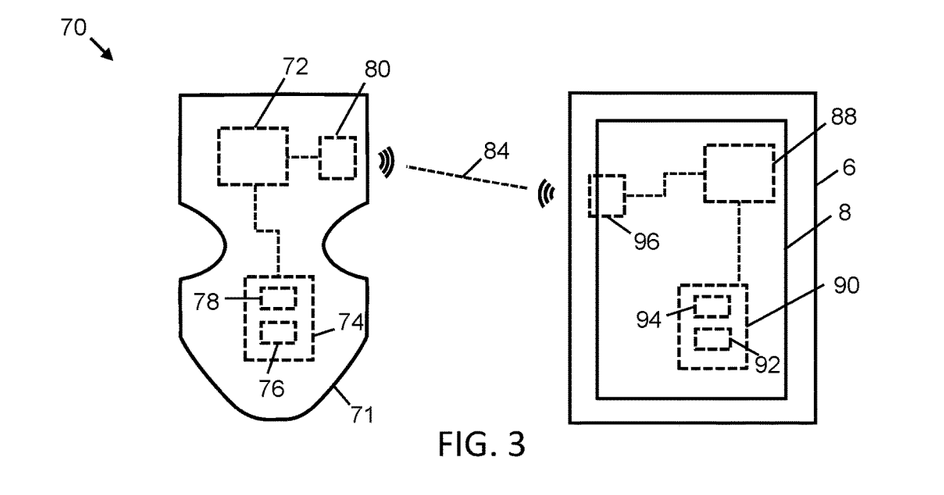
FIG. 3 is a schematic diagram of the system, according to an embodiment of the present invention.

The term "system" when used herein, and not otherwise qualified, refers to an ultrasound imaging system. An example of a system is shown in FIG. 3 and described below.

B. Exemplary Embodiments

Figure 1:
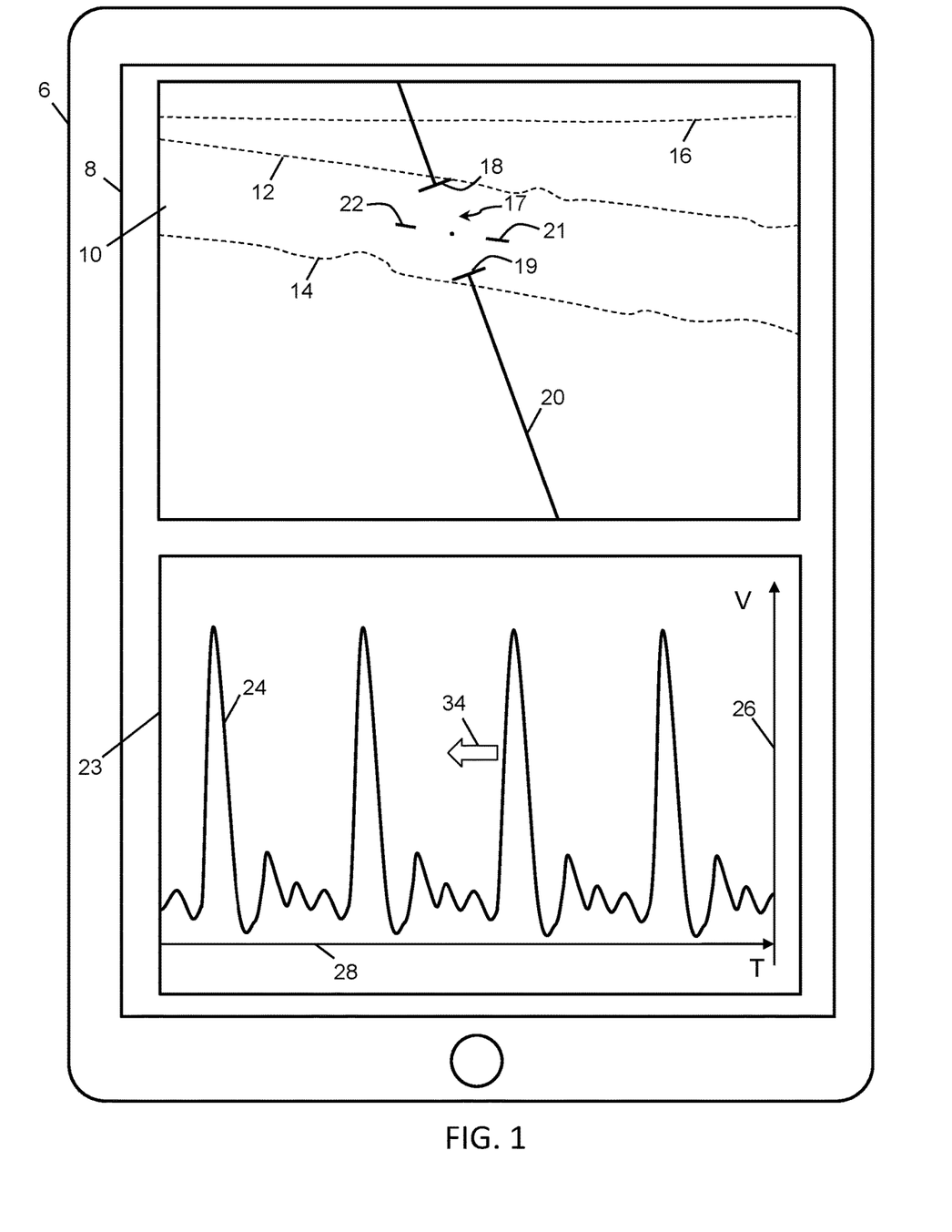
FIG. 1 is a touchscreen user interface showing a B-mode image and a PW Doppler mode spectrum, according to an embodiment of the present invention.

Referring to FIG. 1, an example portable computing device 6 (e.g., a tablet computer, smartphone, or the like), with touchscreen 8 is shown on which a B-mode image 10 is displayed. The B-mode image 10 includes features of a body, such as blood vessel walls 12, 14 and skin 16. Also displayed on the B-mode image 10 is a gate 17 that indicates where a Doppler mode signal in the tissue corresponding to the gate location is obtained. The extent of the gate 17 is defined by ends 18, 19, and the direction of the gate 17 is defined by line 20.

Typically, the blood vessel under observation is not in line with the ultrasound line, and so additional lines next to the gate are shown to indicate a correction angle for the PW Doppler signal. The additional lines should generally be positioned parallel to the vessel walls. The ideal Doppler signal is parallel with the blood flow, and, at the other extreme, a Doppler signal is unobtainable if the blood flow is entirely perpendicular to the ultrasound line. The position and angle of the gate can be adjusted to best orient for the particular ultrasound image, and the correction angle can be set to provide additional information to the system about the angle of the vessel side walls, so that the Doppler signal can be corrected accordingly. In FIG. 1, the correction lines 21, 22 are shown positioned parallel to the walls 12, 14 of the blood vessel being scanned.

Also displayed on the touchscreen 8 is a Doppler mode display portion 23, which shows a corresponding Doppler mode spectrum 24 that represents velocity of blood flow on vertical axis 26 versus time on horizontal axis 28. The displayed spectrum 24 moves to the left of the Doppler mode display portion 23 as time progresses, in the direction of block arrow 34.

The touchscreen 8 therefore displays both a B-mode image 10 and a Doppler mode display portion 23 simultaneously, which is in contrast to a conventional B-mode in which a significantly larger proportion of the touchscreen 8 would be dedicated to the B-mode image and there would be no area reserved for a Doppler mode spectrum.

Figure 2:
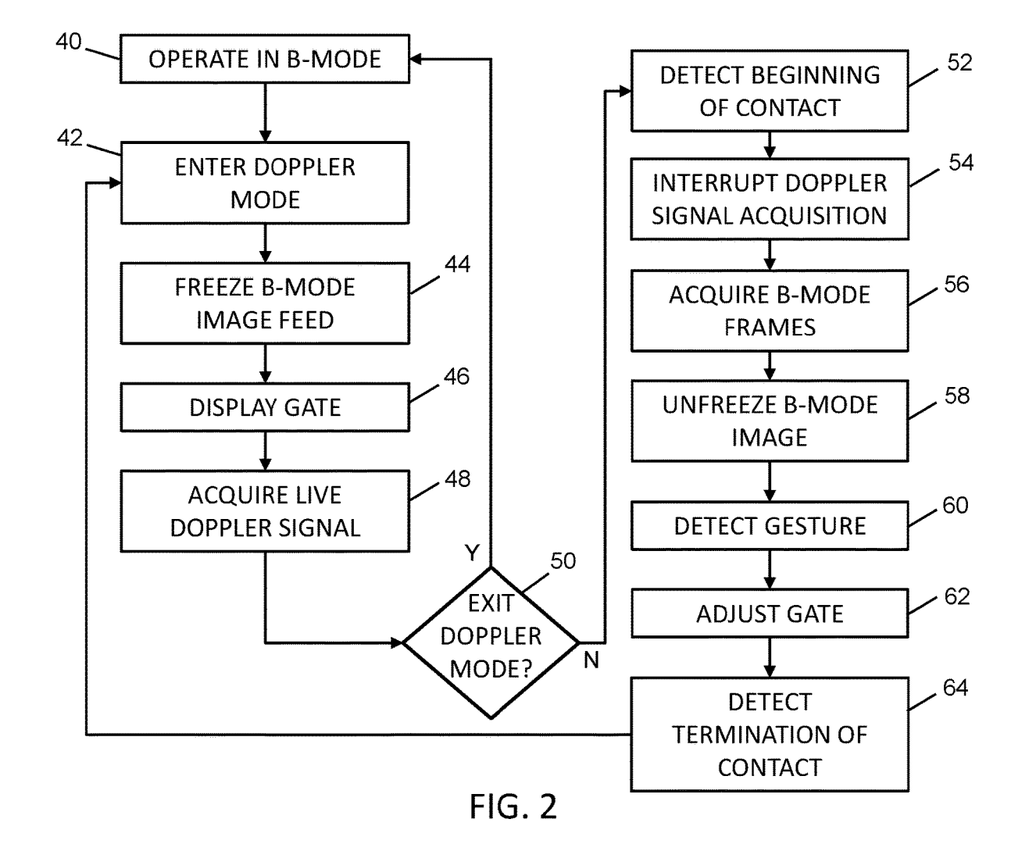
FIG. 2 is a flowchart of a method carried out by the system, according to an embodiment of the present invention.

Referring to FIG. 2, shown there is an example method for switching between a spectral Doppler mode and a B-mode of an ultrasound scanner. In the example embodiment of FIG. 2, at 40, the system may already be operating in a conventional B-mode and the portable computing device 6 may be acquiring a live B-mode image feed from the ultrasound scanner to which it is connected. For example, in this conventional B-mode, the ultrasound scanner may be transmitting and receiving a B-mode ultrasound sequence, and a majority of the touchscreen 8 of the computing device 6 (as shown in FIG. 1) may be used to display the live ultrasound images.

At 42, the system may receive an input that causes it to enter into the spectral Doppler mode. As a result, the ultrasound sequence may be altered so that the acquisition of B-mode image frames stops. At 44, the B-mode image feed may be frozen and the B-mode ultrasound image 10 may be reduced in size for the touchscreen 8 to accommodate the spectral Doppler mode display portion 23. At this point, the displayed B-mode ultrasound image 10 may remain displayed, but in a frozen state.

At 46, the gate 17 may be displayed, superimposed on the now frozen B-mode image 10, and the ultrasound sequence of the ultrasound scanner may be altered to acquire a live Doppler signal stream (act 48). The acquired signal stream is displayed as a live spectrum 24 in the spectral Doppler mode display portion 23 of the touchscreen 8.

At any point in the spectral Doppler mode, an operator of the system may exit the spectral Doppler mode. For example, an exit button may be displayed on the touchscreen 8 that, if activated, exits the spectral Doppler mode. If the exit button is activated (the 'Yes' or 'Y' branch of act 50), the process may revert to act 40 in which a conventional B-mode of the system is entered. However, if there is no contact detected on the exit button (the 'No' or 'N' branch at 50), the system may continue in the spectral Doppler mode.

As noted, when operating in a certain configuration of the spectral Doppler mode (e.g., high PRF or when the gate is positioned deeper into the body), it may be only possible to operate in mono, spectral Doppler mode. Acts 52-64 generally provide an efficient process for switching temporarily to a live B-mode ultrasound sequence, allowing an operator to view live B-mode images, adjust the gate in view of the live B-mode images, then switch back to the mono, spectral Doppler mode.

At 52, while the system is in the spectral Doppler mode, the portable computing device 6 may detect a beginning of a contact on the touchscreen 8. The contact may be, for example, a single, continuous contact that has a longer duration than a typical tap on the touchscreen 8. The contact may be considered to be, for example, a touch and hold, or a touch and drag.

Upon detecting the beginning of the contact, the Doppler signal acquisition may be interrupted (act 54).

Upon detecting the beginning of the contact, the system may also switch temporarily to acquiring live B-mode image frames (act 56), where the ultrasound sequence of the ultrasound scanner may be altered to acquire B-mode lines. At act 58, the B-mode image 10 may be unfrozen. The B-mode of acts 56-58 may be considered to be a B-within-Doppler mode, in that B-mode image frames are acquired and displayed in the user interface similar to a conventional B-mode operation. However, B-mode acquisition in this context is different from the conventional 'B-mode' operation of the ultrasound system at act 40. While both may involve configuring the ultrasound sequence used by the ultrasound scanner to acquire B-mode lines for generating B-mode images without interleaving in spectral Doppler signals, the conventional B-mode operation may allow for more user input to change various imaging parameters such as frequency, gain, or the like. In contrast, the B-mode images shown at acts 56-58 may initially be based on the imaging parameters stored upon entering the Doppler mode at act 42. Also, this B-within-Doppler mode may have fewer options to adjust imaging parameters that would otherwise be adjustable in the conventional B-mode (e.g., imaging depth may be adjustable but gain may not be adjustable).

The user interface layout of the Doppler mode may remain unchanged during acts 56-58. For example, in the example user interface of FIG. 1, the touchscreen 8 may be configured to still have an area for the display of a B-mode image 10 and an area for the Doppler mode display portion 23. The B-mode images acquired as a result of act 56 may be shown where the frozen B-mode image 10 was shown previously. Notably, this is unlike a user interface layout provided in the conventional B-mode, where, for example, the full user interface 8 may display the 2-D B-mode images.

At 60, which occurs while the continuous contact has not yet ended, the portable computing device 6 may detect a gesture made by the continuous contact on the touchscreen 8. In response to detecting the gesture, the gate 17 (as shown in FIG. 1) and its corresponding display on the now live B-mode image 10 are adjusted by the system in accordance with the gesture (act 62). For example, the gate 17 may be adjusted in size, direction, position and/or correction angle. The adjustment of the gate 17 continues in real time as the gesture made by the continuous contact unfolds.

At 64, the portable computing device 6 may detect the termination of the contact on the touchscreen 8. The system may then revert to act 42, in which the Doppler mode is restarted.

By having a gesture that is received as a single, continuous contact with the touchscreen 8, the system can be made to switch from the spectral Doppler mode to the B-mode, adjust the gate 17 and then switch back to the spectral Doppler mode in a single user input. As compared to traditional ultrasound systems that require multiple independent user inputs to perform each of switching to B-mode, adjusting the gate, and switching back to the spectral Doppler mode, the present embodiments provide a more intuitive and efficient user experience.

FIG. 3 is a schematic diagram of an exemplary ultrasound system 70 that may perform the methods described herein. The system 70 may include an ultrasound scanner 71, which may include one or more processors 72 which are operably connected to computer readable memory 74 included in the ultrasound scanner 71. The ultrasound scanner 71 may include computer readable instructions 76 stored in the memory 74 and computer readable data 78, also stored in the memory 74. The memory 74 may be divided into one or more constituent memories, of the same or different types. The processor(s) 72 may execute the computer readable instructions 76 and optionally read the computer readable data 78 to provide, directly or indirectly, one or more functions of the system 70. The ultrasound scanner 71 may include an interface 80, operably connected to the processor(s) 72. The interface 80 may be, for example, a Bluetooth™ or Wi-Fi™ interface, another wireless interface and/or a wired interface that provides a two-way communication link 84 to the portable computing device 6, which may be considered to be part of the system 70.

The portable computing device 6 may be a tablet, a laptop, a smartphone or a desktop computer, for example, or any other electronic device that provides the necessary equivalent functionality to fulfill the requirements of the present embodiments without limitation. The portable computing device 6 may include one or more processors 88 which may be operably connected to computer readable memory 90 included in the portable computing device 6. The portable computing device 6 may include computer readable instructions 92 (e.g., an application) stored in the memory 90 and computer readable data 94, also stored in the memory 90. The memory 90 may be divided into one or more constituent memories, of the same or different types. The processor(s) 8 execute the computer readable instructions 92 and optionally read the computer readable data 94 to provide, directly or indirectly, one or more functions of the system 70. The portable computing device 6 includes a touchscreen 8, operably connected to the processor(s) 88. The portable computing device 6 may also include an interface 96, operably connected to the processor(s) 88. The interface 96 may be, for example, a Bluetooth™ or Wi-Fi™ interface, another wireless interface and/or a wired interface that provides the two-way communication link 84 via a network to the ultrasound scanner 71.

Figure 4A:
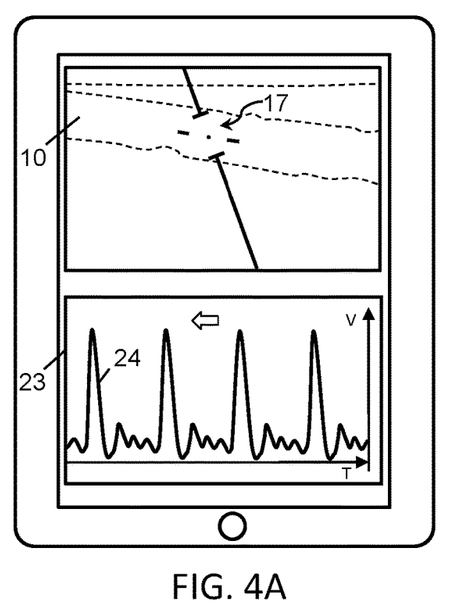
FIGS. 4A-D show a sequence of displays on the user interface as the system is switched between the PW Doppler mode and B-mode, according to an embodiment of the present invention.

Referring to FIGS. 4A-4D, an exemplary sequence of displays on the touchscreen 8 is shown as the method of FIG. 2 is performed. Prior to the screenshot of FIG. 4A, the system may be operating in a conventional B-mode operation (act 40 of FIG. 2). The system may then receive input to switch to a spectral Doppler mode (e.g., through navigation of a menu or some other user interface mechanism). In FIG. 4A, the system 70 is in the spectral Doppler mode (act 42 of FIG. 2). The B-mode image 10 is frozen (act 44 of FIG. 2), as indicated in FIG. 4A by it being drawn in light dashed lines. The gate 17 is shown superimposed on the frozen B-mode image 10 (act 46 of FIG. 2). The spectrum 24, in the Doppler mode display portion 23, is shown in a bold line as it is live and the live Doppler signal is being acquired (act 48 of FIG. 2).

Figure 4B:
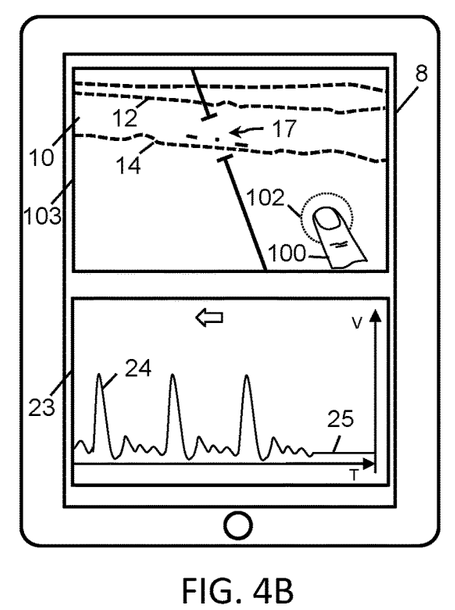

In FIG. 4B, the system 70 has been temporarily switched to acquire B-mode image frames by a finger 100 of the operator beginning a continuous contact 102 with the touchscreen 8 (act 52 of FIG. 2). The operator may have initiated this action for various reasons, for example, because the body being scanned has moved, the ultrasound scanner 71 has moved, and/or the spectrum 24 has changed in its displayed characteristics (e.g., diminished in amplitude). The mono, Doppler signal acquisition may then be interrupted (act 54 of FIG. 2) to allow for B-mode frames to be acquired (act 56 of FIG. 2). Correspondingly, the frozen B-mode image 10 may be unfrozen (act 58 of FIG. 2) and live B-mode images 10 may be displayed (this is shown as the B-mode image 10 having bold dashed lines in FIG. 4B). The gate 17 is shown superimposed on the frozen B-mode image 10 in the same relative position in the display area 103 as it was in FIG. 4A. However, in the example screenshot of FIG. 4B, it can be seen that the vessel on which the gate 17 was centered in FIG. 4A has now shifted in the live ultrasound image 10 so that the gate 17 is no longer in the optimal centered position. As a result, the gate 17 is no longer set in the originally desired location and orientation, and the Doppler mode signal that was being acquired immediately prior to switching to the B-mode was therefore likely to be less accurate than it could have been.

Referring still to FIG. 4B, it can also be seen that the spectrum 24 in the Doppler mode display portion 23 is no longer acquiring a live signal (as shown in a light line in FIG. 4B in contrast to the bold line showing the live spectrum in FIG. 4A). A flatline portion 25 of the spectrum 24 in FIG. 4B also shows that the acquisition of the Doppler signal has been interrupted.

Figure 4C:
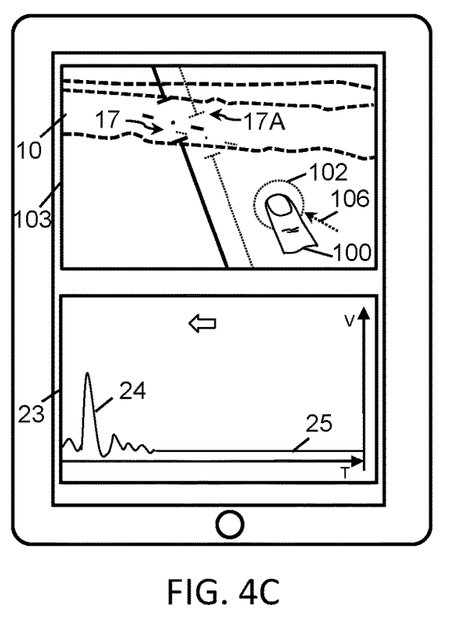

In FIG. 4C, a gesture is detected (act 60 of FIG. 2) and the continuous contact 102 made by the operator's finger 100 has moved along path 106 from its original position in FIG. 4B, without the contact being lifted or terminated. As a result, the system 70 continues to acquire B-mode frames and the B-mode image 10 remains live. Also, the position of the gate 17 (as shown in solid lines) has been adjusted (act 62 of FIG. 2). As shown, the gate 17 has been moved in accordance with the movement or gesture made by the contact 102 from its original position 17A relative to the display area 103 (the original position 17A being shown in lighter, dotted lines). In this manner, the gesture, or movement, of the continuous contact 102 results in the gate 17 being adjusted back to a desired position relative to the internal features of the anatomy being detected by the ultrasound scanner 71 (e.g., with the gate 17 being centered on the vessel). While the continuous contact 102 proceeds, the spectral Doppler mode remains interrupted. In the Doppler mode display portion 23 of the user interface, the spectrum 24 remains frozen while still moving to the left and the flatline portion 25 increasing in length.

Figure 4D:
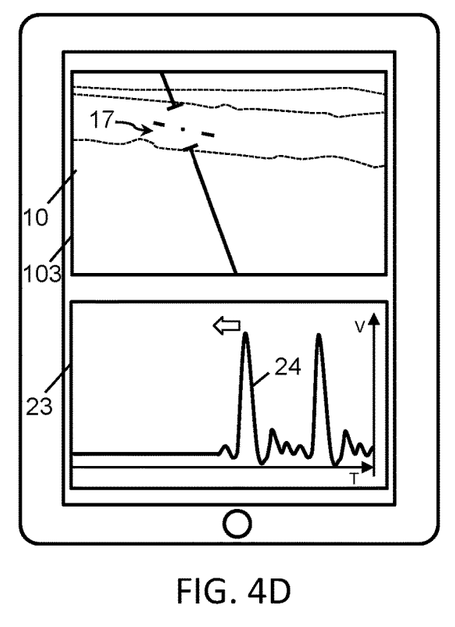

In FIG. 4D, the continuous contact 102 has terminated at its position as shown in FIG. 4C (act 64 of FIG. 2). The system 70 returns to the Doppler mode (act 42 of FIG. 2), and the B-mode image feed is once again frozen (act 44 of FIG. 2). In the example screenshot of FIG. 4D, this is shown with the B-mode image having lighter, dotted lines similar to FIG. 4A. The gate 17 remains superimposed on the B-mode image 10 (act 46 of FIG. 2) in the same position as it was left in FIG. 4C relative to the display area 103. In the Doppler mode display portion 23, the Doppler spectrum 24 reverts to a live signal (act 48 of FIG. 2). The live spectrum is shown in a bold line in FIG. 4D, which, compared to the spectrum in FIG. 4C, has a larger amplitude due to the gate now having been repositioned to its optimal location.

FIGS. 4A-4D thus show a sequence of actions for detection of contact of an area on the touchscreen, and, upon the contact occurring, the B-mode image becoming live and the spectral Doppler mode being interrupted. During the contact, the operator can drag the gate to the desired location on the live B-mode image. Once the gate is located as desired, the operator can release the contact, the B-mode image freezes and the spectral Doppler mode returns to a live state. This can all be accomplished with a single, simple gesture, making the gate positioning more user friendly than traditional methods.

Figure 5:
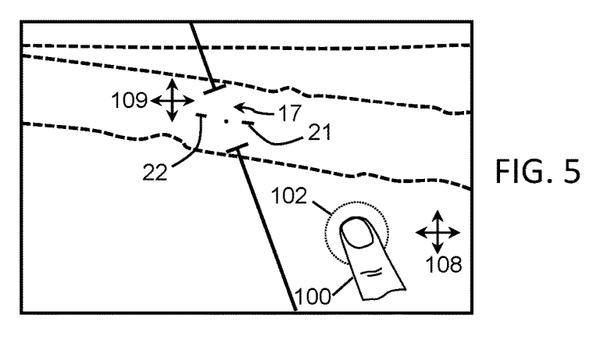
FIG. 5 is an example of how a single, continuous contact with the touchscreen can be used to adjust the gate, according to an embodiment of the present invention.

Referring to FIG. 5, shown there is an example embodiment of how the continuous contact 102 with the touchscreen 8 at a single location may be used to adjust the gate 17 according to the sequence of screenshots shown in FIGS. 4A-4D. In the illustrated example, the touch location 102 is on the B-mode image but not on the gate 17 itself. However, in various embodiments, the continuous contact may be received on the gate 17 itself, close to the gate 17, elsewhere on the B-mode ultrasound image 10, and/or on another area of the touchscreen 8. The operator's finger 100, when in continuous contact 102 with the touchscreen 8 may move, for example, in directions 108, e.g., vertically, horizontally, diagonally (or any other direction in that plane) on the surface of the touchscreen 8. In accordance with this movement of the continuous contact 102, the gate 17 may move in corresponding directions 109, e.g., vertically, horizontally, diagonally (or any other direction in that plane). In various embodiments, the movement of the gate 17 may be at the same rate at which the continuous contact 102 moves or be faster or slower than the rate of movement of the continuous contact 102. For example, the rates at which the continuous contact 102 and the gate 17 move may be scaled relative to each other by a proportion other than 1:1. In this basic example, the gate 17 moves as a whole, without its orientation or size being adjusted, and without the angle of the correction lines 21, 22 being adjusted.

Notably, the user interface screenshots shown in FIGS. 4A-4D, and FIG. 5 are for an example embodiment where the gate 17 is simply repositioned without any other aspects of the gate (e.g., steering angle, correction angle) otherwise being adjusted. However, in various embodiments, user interface inputs for adjusting other aspects of the gate 17 may also be possible.

Figure 6:
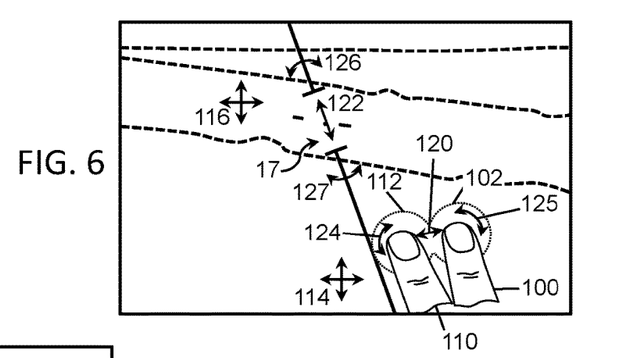
FIG. 6 is an example of how a double, continuous contact with the touchscreen can be used to adjust the gate, according to an embodiment of the present invention.

Referring to FIG. 6, shown there is an example embodiment where finger 100 with continuous contact 102 and finger 110 with continuous contact 112 can be used as double continuous contact locations on the touchscreen 8 to adjust the gate 17. For example, the two points of continuous contact 102, 112 may be moved together in directions 114, e.g., vertically, horizontally diagonally (or in any other direction on that plane) on the surface of the touchscreen 8. In accordance with this movement of the double continuous contact 102, 112, the gate 17 may move in corresponding directions 116, e.g., vertically, horizontally diagonally (or in any other direction on that plane) at the same rate at which the double continuous contact 102, 112 moves. In other embodiments, the rates at which the double continuous contact 102, 112 and the gate 17 move may be scaled relative to each other by a proportion other than 1:1.

In another example, the two points of continuous contact 102, 112 may be moved towards or away from each other in a pinch or spread gesture indicated by the arrows 120. In synchronization with this pinch or spread gesture 120 of the double continuous contact 102, 112, the gate 17 may correspondingly be reduced or lengthened according to arrows 122, in proportion to the rate at which the separation of the two continuous contacts 102, 112 changes.

In a further example, the two points of continuous contact 102, 112 may be rotated relative to each other as indicated by the arrows 124, 125. In accordance with this rotation gesture 124, 125 of the double continuous contact 102, 112, the angular orientation (e.g., ultrasound line) of the gate 17 may be changed according to arrows 126, 127, in proportion to the rate at which the two continuous contacts 102, 112 rotate.

In various embodiments, one of the two continuous contacts 102, 112 may then be terminated so that only one point of continuous contact continues, such as continuous contact 102. The correction angle of the correction lines 21, 22 may then be adjusted. For example, referring back to FIG. 5, the remaining continuous contact 102 may be used to adjust only the angle of orientation of the correction lines 21, 22 (e.g., a drag gesture of the remaining continuous contact 102 may rotate the correction lines 21, 22 in clockwise direction, and a drag gesture in the opposite direction may rotate the correction lines 21, 22 in a counter-clockwise direction).

Figure 7:
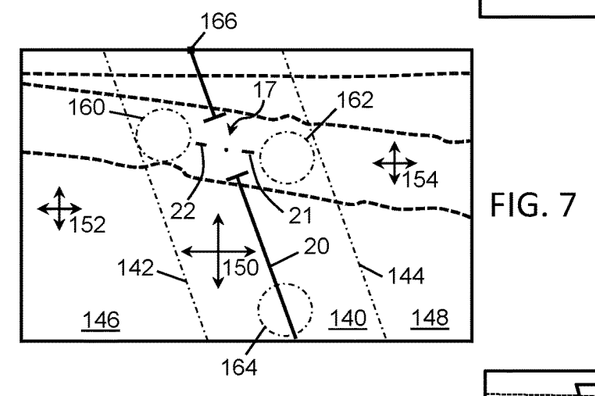
FIG. 7 is an example of how different regions of contact with the touchscreen can be used to adjust the gate, according to an embodiment of the present invention.

Referring to FIG. 7, shown there is an example embodiment where the area of the touchscreen 8 on which the B-mode image 10 is displayed may be divided into different regions, where the continuous contact in each of the regions has a different function. For example, the B-mode image 10 may be divided into a middle area 140 delimited by lines 142, 144, a left area 146 to the left of line 142, and a right area 148 to the right of line 144. Within the middle area 140, if the continuous contact is moved in directions 150, the gate 17 may move as a whole in corresponding directions with a coarse resolution (e.g., with the gate 17 moving relatively large distances in comparison to the movement of the continuous contact with the touchscreen 8). However, if the continuous contact is moved in directions 152 in the left area 146 or directions 154 in the right area 148, the gate 17 may move as a whole in corresponding directions with a fine resolution (e.g., with the gate 17 moving relatively shorter distances in comparison to the movement of the gate 17 when analogous continuous contact with the touchscreen 8 is received in the middle area 140).

In this example embodiment, when the gate 17 moves as a whole, it may maintain its angular orientation, size and correction angle. However, in some embodiments, there may also be provided zones 160, 162 of the B-mode image 10 to the left and right of the correction lines 22, 21 respectively, which, when continuous contact is made therewith, singly or doubly, allows the correction angle of the gate 17 to be adjusted. To change the steering angle of the line 20 that the gate 17 is on, a drag gesture on the bottom of the B-mode image 10 in zone 164 (e.g., to the left or right) may result in the line 20 pivoting around what becomes a fixed top endpoint 166 of the line 20.

As it can be readily understood, there are many possible dimensions, relative dimensions, configurations and permutations of the different contact areas of the B-mode image 10 and the zones therein, and the associated ways in which the gate 17 may be adjusted.

In some embodiments, a delay may be implemented in the operation of the system 70 before switching back to the spectral Doppler mode after termination of the continuous contact, so that a series of continuous contacts may be employed to fully adjust the gate 17 as desired by the operator. For example, the operator may adjust the position of the gate with one continuous contact, terminate the continuous contact, and then quickly start another continuous contact to adjust the angle of the ultrasound line 20 that the gate 17 is on. The Doppler mode would then be restarted only after both of these continuous contacts have terminated. In various embodiments, this delay may configured to be between 50 milliseconds to 1 second, for example.

In the discussion above, the present embodiments have generally been described in the context of a combined B-mode and PW Doppler imaging mode. As noted, such a combination mode may run in duplex by default by interleaving or interrupting temporarily the PW acquisition sampling signals. However, due to transmit/receive timing constraints (e.g., when the PRF is too high and/or if the position of the gate is too deep), PW Doppler mode cannot always be run simultaneously with the acquisition of B-mode frames. The ultrasound scanner can then revert to the mono PW Doppler mode (e.g., only PW samplings are obtained) where the embodiments described herein may be deployed.

However, in addition to the combination B-mode and PW Doppler mode, there are other combination modes in which the present embodiments can be used. For example, some ultrasound systems may allow for three different imaging modes to be combined together. Examples of these include adding a further mode to the B/PW combination already discussed: e.g., adding a Color Doppler or Power Doppler mode. This results in additional combination modes that combine: B-mode, PW Doppler, and Color Doppler together (B/PW/Color); or B-mode, PW Doppler, and Power Doppler together (B/PW/Power).

In these triplet combination modes, it may be possible to operate in a triplex mode where all three different types of ultrasound signals are acquired in a full imaging sequence. However, since there is an additional type of ultrasound signal being acquired in addition to the B-mode and PW Doppler signals, the physical timing constraints discussed above are even more pronounced. This makes triplex mode difficult to implement. For example, since either Color Doppler or Power Doppler have their own unique PRF values versus PW Doppler PRF values, the operator would have to be careful to consider what PRFs to choose when operating in these modes. Also, since all three types of ultrasound signals are needed to be acquired, a limited range of PRF values for the PW Doppler mode may be available and/or there may be frame rate limitations in the triplex mode.

To offer a full range of PRFs and to provide a sufficiently high frame rate when viewing live 2D images, the system 70 may allow for a toggling between mono PW Doppler on the one hand, and a duplex operation of the remaining two imaging modes on the other hand. For example, in the B/PW/Color combination mode, this toggling would be between a mono PW Doppler mode and a 2D-mode that is a combined, duplex B-mode/Color Doppler mode. Similarly, in the B/PW/Power combination mode, this toggling would be between a mono PW Doppler mode and a 2D-mode that is a combined, duplex B-mode/Power Doppler mode.

The embodiments described herein may generally be used to toggle away from a spectral Doppler mode such as mono PW Doppler mode. This may include toggling from a mono PW Doppler mode to dedicated B-mode frame acquisition (as discussed above); but it may also include in various embodiments, toggling to a duplex B/Color combination mode, and/or to a duplex B/Power combination mode. Indeed, the embodiments described herein may be particularly desirable when toggling to a B/Color or a B/Power combination mode because of the noted PRF and frame rate constraints of trying to squeeze three different types of ultrasound signals into a triplex mode. Moreover, toggling between a mono PW Doppler mode to another duplex, combination mode (whether B/Color or B/Power) may allow the operator to better visualize the location of the fluid flow (e.g., because of the presence of the Color). This may allow for a more accurate placement of the PW Doppler gate as compared to simply placing the gate on a simple B-mode image, where the fluid flow locations may potentially be confused with other dark spots on the B-mode image.

Referring briefly back to FIG. 2 above, where act 56 is described above as being for acquiring B-mode frames, in the context of the toggling between a mono, spectral Doppler mode and a combined B/Color mode, act 56 may involve acquiring B-mode frames and Color Doppler signals in duplex. Similarly, in the context of toggling between a mono, spectral Doppler mode and a combined B/Power mode, act 56 may involve acquiring B-mode frames and Power Doppler signals in duplex. At act 58 of FIG. 2, corresponding Color or Power signals can be displayed on the live B-mode images. The comments in this paragraph may also apply to acts 196 and 198 in FIG. 10 below.

Due in part to the difficulty with low frame rates and limited availability of PW Doppler PRFs in triplex mode (either in B/PW/Color or B/PW/Power combination modes), some ultrasound systems may configure the default operation of these 'triple' combination modes to toggle between the mono PW Doppler and the duplex modes discussed above (e.g., the combined B-mode/Color Doppler mode, or the combined B-mode/Power Doppler mode). The embodiments described herein thus may be particularly desirable in these contexts because they would be deployed in the default operation of these 'triple' combination modes. For example, in the default operation of these modes, it would be necessary to interrupt the mono PW Doppler signal acquisition in favour of a live, combined B-mode/Color Doppler image or a live, combined B-mode/Power Doppler image to adjust or confirm the position of the PW Doppler gate.

Figure 8:
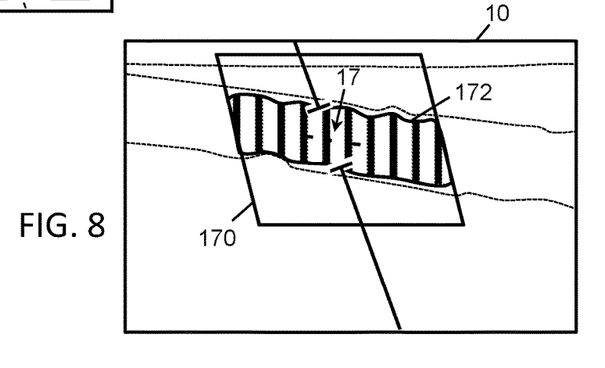
FIG. 8 is an example of elements in a combination mode that can be adjusted according to an embodiment of the present invention.

Referring to FIG. 8, shown there is an example embodiment of elements that can be adjusted in a B/PW/Color combination mode of the ultrasound scanner 71. As shown, superimposed on the B-mode image 10 is a color box 170 within which the color mode signal 172 is obtained and displayed. When the B-mode image 10 and the color mode signal 172 are live, the PW Doppler signal is interrupted, and the gate 17 and/or color box 170 may be adjusted. When the PW Doppler is live, the B-mode image 10 is frozen and the appearance of color from the color-mode signal 172 may be removed.

The embodiments described herein have generally been discussed in the context of switching/toggling between a spectral Doppler mode (such as mono PW Doppler) and other imaging modes that involve the acquisition of B-mode image frames (e.g., either acquisition of B-mode alone, or duplex acquisition of B-mode/Color Doppler, or duplex acquisition of B-mode/Power Doppler). However, in some other embodiments, the principle of the present embodiments may also be used to switch between other modes of operation of an ultrasound scanner.

For example, other combination modes include B/CW (continuous wave), B/CW/Color Doppler and B/CW/Power Doppler. CW would generally not be operated in duplex with other types of ultrasound signals because it is continuously transmitting and receiving Doppler signals. However, it may be possible to use the embodiments described herein to operate CW in mono and toggle to other modes involving the acquisition of B-mode images (e.g., a combined B/Color Doppler mode, or a combined B/Power Doppler mode).

In some embodiments, it may be possible to use the systems and methods described herein in imaging modes that do not involve spectral Doppler at all. For example, the embodiments described herein may generally be used to switch between any one-dimensional (1-D) ultrasound imaging mode that requires placement of a line and/or gate and any two-dimensional (2-D) ultrasound imaging mode that would help the operator identify the anatomy on which to place the 1-D line and/or gate.

For example, M-Mode (e.g., Motion-mode) provides a time motion display of ultrasound signals along a chosen ultrasound line. Traditionally, M-mode is operated in duplex where B-mode signals are interleaved with the M-mode sampling signals. However, it may be possible for M-Mode to run as a sole spectrum where only M-mode sampling signals are acquired without any B-mode signals being acquired. In these instances, the user interface layout may vary from a typical M-mode user interface layout. For example, a frozen B-mode image may be displayed while the M-mode spectrum is being displayed, or in another example, the B-mode image may be removed from the display altogether so that more of the screen can show the M-mode spectrum. This type of mono M-mode operation may be desirable due to constraints of the computing device 6 (e.g., limited screen size may make it suitable to only show the spectrum of the M-mode). Additionally or alternatively, the mono M-mode operation may be suitable if a particularly high average repetition period of the M-mode line is desired. In mono M-mode, the embodiments described herein may be used to toggle between (i) acquiring B-mode ultrasound signals and displaying a live B-mode image (e.g., to assist with placement of the M-mode acquisition line), and (ii) acquiring the M-mode sample signals in mono and displaying the live M-mode spectrum.

In another example, some ultrasound systems have elastography modes that provide a map and/or measurement of tissue stiffness (e.g., using shear wave vibrations and/or acoustic radiation force imaging (ARFI)). In these modes, a region of tissue may be continuously measured with outputs being displayed in real-time to the user. In order to achieve proper targeting within the tissue, it may be helpful to provide a "gate" to position the desired elastography measurement area. The systems and methods described herein may be used in these elastography modes to assist in the positioning of the gate by providing a mechanism to toggle between the live elastography measurement mode and the live B-mode image (e.g., which may allow the operator confirm the position of the gate and/or reposition the gate).

In a further example, some ultrasound systems may provide 3-dimensional (3D) imaging modes where 3D images are acquired by scanning a region of the body at a high resolution using B-mode like slices. Generally, the 3D image is acquired at a 3D region of interest (ROI) that is identified by the operator. While the 3D image is being displayed, the acquisition of regular 2D B-mode images may be paused. In various embodiments, the methods and systems described herein may be used to toggle between (i) acquiring and display of the 3D images (e.g., while the B-mode image is paused), and (ii) the acquisition and display of a live 2D B-mode image (e.g., for placement or repositioning of the 3D ROI). For example, in some embodiments, the touching of a frozen B-mode image in a 3D imaging user interface may re-activate the ROI placement on live B mode image.

Figure 9:
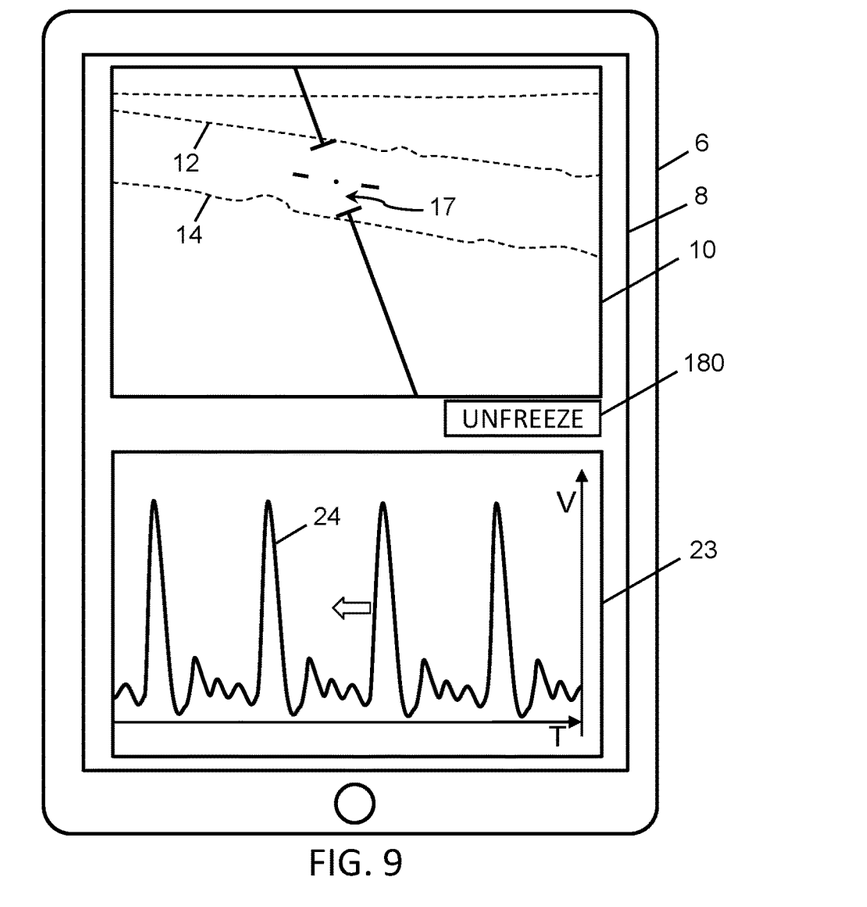
FIG. 9 is an example of a user interface with a temporary unfreeze button, according to an embodiment of the present invention.

Referring to FIG. 9, shown there is another example embodiment in which the user interface shown on the portable computing device 6 with touchscreen 8 has an unfreeze button 180 is displayed beneath the B-mode image 10. The user interface is that shown while the system is operating in a spectral Doppler mode. As such, also displayed on the touchscreen 8 is the Doppler mode display portion 23. In this embodiment, the unfreeze button 180 may be a temporary unfreeze button. For example, when this button is activated (e.g., by a tap), it may have the effect of temporarily unfreezing the B-mode image 10 for a predetermined duration of time (e.g., 1-2 seconds). While the B-mode image 10 is unfrozen, the Doppler mode spectrum 24 is interrupted. After the predetermined duration, the spectral Doppler mode can be restarted automatically.

Figure 10:
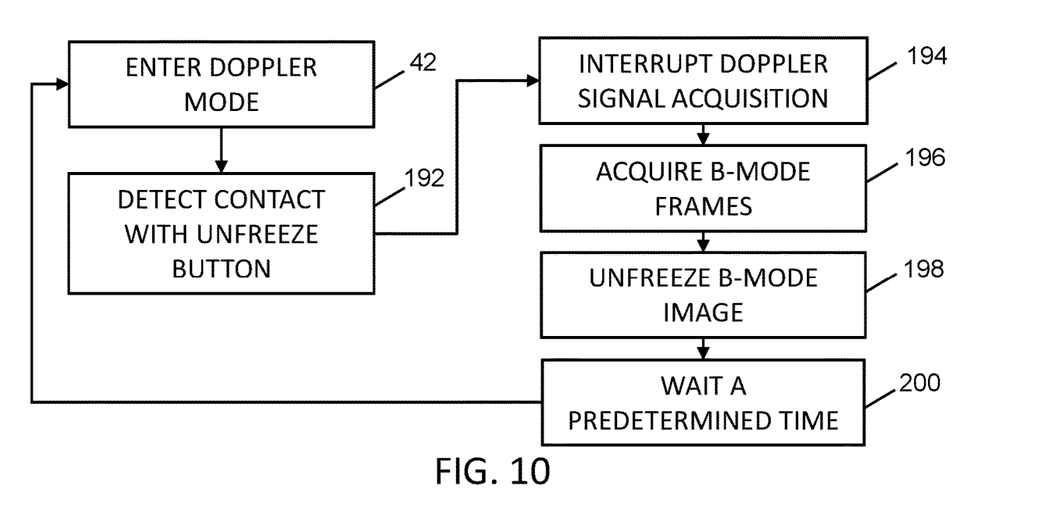
FIG. 10 is a flowchart of a method carried out by the system using the temporary unfreeze button, according to an embodiment of the present invention.

Referring to FIG. 10, shown there is a flowchart indicating use of the temporary unfreeze button 180 of the user interface show in FIG. 9. At 42, the system 70 may enter the spectral Doppler mode. At 192, the portable computing device 6 may detect a contact such as tap or touch on the unfreeze button 180. At 194, the system 70 may interrupt the spectral Doppler mode signal acquisition and, at 196, acquire B-mode frames. In conjunction with this, the system 70 may unfreeze the B-mode image 10, at 198, and then wait a predetermined duration of time at 200 before reverting back to act 42. At 42, the spectral Doppler mode can be reentered automatically without the computing device 6 receiving any further user input.

In various embodiments, the embodiments of FIGS. 9 and 10 may be desirable to provide the operator with a way of quickly checking and/or confirming the position of the gate 17 relative to the live position of the ultrasound transducer and its position on the body. This may or may not involve adjustment of the position of the gate 17.

In various embodiments, the embodiment of FIGS. 9 and 10 may be provided additionally or alternatively to the embodiments described above (e.g., the method of FIG. 2). For example, the method of FIG. 10 may be operational in parallel with the flowchart of FIG. 2. In an example embodiment, it may be possible to provide a system with the user interface shown in FIG. 9 that can interrupt the Doppler signal in different ways, including: (i) temporarily, upon either activation of the unfreeze button 180; or (ii) until a termination of a continuous contact with the touchscreen once the beginning of a continuous touch on a location of the displayed B-mode image 10 is detected.

C. Variations

Variations of the embodiments described herein are possible. While the description has been largely given in relation to the PW Doppler mode, the present embodiments may apply to toggling between other ultrasound modes as described herein.

Embodiments of the invention may be implemented using specifically designed hardware, configurable hardware, programmable data processors configured by the provision of software (which may optionally include 'firmware') capable of executing on the data processors, special purpose computers or data processors that are specifically programmed, configured, or constructed to perform one or more acts or steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, main computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The embodiments may also be provided in the form of a program product. The program product may include any non-transitory medium which carries a set of computer-readable instructions which, when executed by a data processor, cause the data processor to execute a method of the present embodiments. Program products according to the present embodiments may be in any of a wide variety of forms. The program product may include, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. software, processor, support assembly, valve device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. For example, various example ultrasound images and user interface screenshots are shown in the drawings, but they may not be drawn to scale. The technology provided herein can be applied to systems other than the example systems described above. Many alterations, modifications, additions, omissions and permutations are possible within the practice of this present embodiments. The present embodiments include variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

In some embodiments, the components of the systems and apparatuses may be integrated or separated. Moreover, the operations of the systems and apparatuses disclosed herein may be performed by more, fewer, or other components and the methods described may include more, fewer, or other steps. In other instances, well known elements have not been shown or described in detail and repetitions of steps and features have been omitted to avoid unnecessarily obscuring the invention. Screen shots may show more or less than the examples given herein. Accordingly, the specification is to be regarded in an illustrative, rather than a restrictive, sense.

It is therefore intended that the appended claims and claims hereafter introduced are interpreted to include all such modifications, permutations, additions, omissions and subcombinations as may reasonably be inferred. The scope of the claims should not be limited by the embodiments set forth in the examples but should be given the broadest interpretation consistent with the description as a whole.

D. Interpretation of Terms

Unless the context clearly requires otherwise, throughout the description and the claims, the following applies:

In general, unless otherwise indicated, singular elements may be in the plural and vice versa with no loss of generality. The use of the masculine can refer to masculine, feminine or both.

The terms "comprise", "comprising" and the like are to be construed in an inclusive sense, as opposed to an exclusive or exhaustive sense, that is to say, in the sense of "including, but not limited to".

The terms "connected", "coupled", or any variant thereof, means any connection or coupling, either direct or indirect, between two or more elements; the coupling or connection between the elements can be physical, logical, or a combination thereof.

The words "herein," "above," "below" and words of similar import, when used in this application, refer to this application as a whole and not to any particular portions of this application.

The word "or" in reference to a list of two or more items covers all of the following interpretations of the word: any of the items in the list, all of the items in the list and any combination of the items in the list.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Where numerical values are given, they are specified to the nearest significant figure.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

E. Claim Support

In a first broad aspect of the present disclosure, there is provided a method for switching an ultrasound scanner between a spectral Doppler mode ("SD-mode") and a two-dimensional (2D) ultrasound imaging mode ("2D-mode") comprising: displaying, on a touchscreen that is communicatively connected to the ultrasound scanner, while the ultrasound scanner is operating in the SD-mode, a display comprising: a frozen 2D-mode ultrasound image; a gate that corresponds to the SD-mode, the gate superimposed on the frozen 2D-mode ultrasound image; and a live SD-mode ultrasound spectrum that corresponds to the gate; receiving an input to adjust the gate, the input comprising a continuous contact with the touchscreen; switching, by a processor, in response to detecting a beginning of the continuous contact, the ultrasound scanner from the SD-mode to the 2D-mode; adjusting, by the processor in response to the switching, the display to unfreeze the frozen 2D-mode ultrasound image;

detecting, by the processor, during the continuous contact, a characteristic of the continuous contact; and adjusting, by the processor, the gate displayed on the unfrozen 2D-mode ultrasound image in accordance with the characteristic.

The method may comprise: detecting, by the processor, a termination of the continuous contact; switching, in response to the termination, the ultrasound scanner from the 2D-mode to the SD-mode, in which the ultrasound scanner obtains an SD-mode ultrasound signal corresponding to the adjusted gate; and adjusting the display, in response to the termination, to: refreeze the 2D-mode ultrasound image; and display a live SD-mode ultrasound spectrum that corresponds to the adjusted gate.

The method may comprise: displaying, on the touchscreen, an unfreeze button; detecting a contact with the unfreeze button; switching, by the processor, in response to detecting the contact, the ultrasound scanner from the SD-mode to the 2D-mode for a predetermined duration of time; adjusting, by the processor, the display to unfreeze the frozen 2D-mode ultrasound image for the predetermined duration of time; and switching, by the processor, the ultrasound scanner from the 2D-mode to the SD-mode after the predetermined duration of time.

In some embodiments, the predetermined duration of time is longer than a duration of the contact.

In some embodiments, the characteristic of the continuous contact with the touchscreen comprises a drag gesture, and a position of the displayed gate is continuously updated during the drag gesture to track a displacement of the drag gesture.

In some embodiments, the characteristic of the continuous contact with the touchscreen comprises a drag gesture, and an angular orientation of the displayed gate is continuously updated during the drag gesture in proportion to a displacement of the drag gesture.

In some embodiments, the characteristic of the continuous contact with the touchscreen comprises a drag gesture, and a size of the displayed gate is continuously updated during the drag gesture in proportion to a displacement of the drag gesture.

In some embodiments, the continuous contact with the touchscreen comprises two contact points and the characteristic of the continuous contact is a drag gesture of the two contact points, and a position of the displayed gate is continuously updated during the drag gesture to track a displacement of the two contact points.

In some embodiments, the continuous contact with the touchscreen comprises two contact points and the characteristic of the continuous contact is a rotation gesture, and an angular orientation of the displayed gate is continuously updated during the rotation gesture in proportion to an angle of rotation of the rotation gesture.

In some embodiments, the continuous contact with the touchscreen comprises two contact points and the characteristic of the continuous contact is a spread or pinch gesture, and a size of the displayed gate is continuously updated during the spread or pinch gesture in proportion to a change in separation of the two contact points.

In some embodiments, the input begins on the frozen 2D-mode ultrasound image and continues on the unfrozen 2D-mode ultrasound image.

In some embodiments, the input is not on the displayed gate.

In some embodiments, the gate is adjusted more coarsely when the beginning of the continuous contact is at a first location on the touchscreen than when the beginning of the continuous contact is at a second location on the touchscreen.

In some embodiments, the SD-mode is a pulsed-wave Doppler mode. In some embodiments, the 2D-mode may be one of: B-mode, a combined B-mode/Color Doppler mode, or a combined B-mode/Power Doppler mode.

In some embodiments, the method may involve adjusting the display to show a flatline SD-mode spectrum when the 2D-mode image is unfrozen.

In another broad aspect of the present disclosure, there is provided an ultrasound system that switches between a spectral Doppler mode ("SD-mode") and a two-dimensional (2D) ultrasound imaging mode ("2D-mode") comprising: an ultrasound scanner; a touchscreen; a processor that is communicatively connected to the ultrasound scanner and operatively connected to the touchscreen; non-transitory computer readable memory storing computer readable instructions, which, when executed by the processor cause: the touchscreen to display, while the ultrasound scanner is operating in the SD-mode: a frozen 2D-mode ultrasound image; a gate that corresponds to the SD-mode, the gate superimposed on the frozen 2D-mode ultrasound image; and a live SD-mode ultrasound spectrum that corresponds to the gate; the touchscreen to receive an input to adjust the gate, the input comprising a continuous contact with the touchscreen; the ultrasound scanner to switch from the SD-mode to the 2D-mode, in response to detecting a beginning of the continuous contact; the touchscreen to unfreeze the frozen 2D-mode ultrasound image, in response to the switch; the touchscreen to detect, during the continuous contact, a characteristic of the continuous contact; and the touchscreen to adjust the gate displayed on the unfrozen 2D-mode ultrasound image in accordance with the characteristic.

In some embodiments, the computer readable instructions, when executed by the processor, cause: the touchscreen to detect a termination of the continuous contact; the ultrasound scanner to switch, in response to the termination, from the 2D-mode to the SD-mode, in which the ultrasound scanner obtains a SD-mode ultrasound signal corresponding to the adjusted gate; and the touchscreen to adjust, in response to the termination, the display to: refreeze the 2D-mode ultrasound image; and display a live SD-mode ultrasound spectrum that corresponds to the adjusted gate.

In some embodiments, the characteristic of the continuous contact with the touchscreen comprises: a first drag gesture, wherein a position of the displayed gate is continuously updated during the first drag gesture to track a displacement of the first drag gesture; a second drag gesture, wherein an angular orientation of the displayed gate is continuously updated during the second drag gesture in proportion to a displacement of the second drag gesture; a third drag gesture, wherein a size of the displayed gate is continuously updated during the third drag gesture in proportion to a displacement of the third drag gesture; two first contact points, wherein the characteristic of the continuous contact is a fourth drag gesture of the two first contact points, and the position of the displayed gate is continuously updated during the fourth drag gesture to track a displacement of the two first contact points; two second contact points, wherein the characteristic of the continuous contact is a rotation gesture, and the angular orientation of the displayed gate is continuously updated during the rotation gesture in proportion to an angle of rotation of the rotation gesture; or two third contact points, wherein the characteristic of the continuous contact is a spread or pinch gesture, and a size of the displayed gate is continuously updated during the spread or pinch gesture in proportion to a change in separation of the two third contact points.

In another broad aspect of the present disclosure, there is provided a portable computing device that switches an ultrasound scanner between a spectral Doppler mode ("SD-mode") and a two-dimensional (2D) ultrasound imaging mode ("2D-mode") comprising: a touchscreen; a processor that is communicatively connected to the ultrasound scanner and operatively connected to the touchscreen; non-transitory computer readable memory storing computer readable instructions, which, when executed by the processor cause: the touchscreen to display, while the ultrasound scanner is operating in the SD-mode: a frozen 2D-mode ultrasound image; a gate that corresponds to the SD-mode, the gate superimposed on the frozen 2D-mode ultrasound image; and a live SD-mode ultrasound spectrum that corresponds to the gate; the touchscreen to receive an input to adjust the gate, the input comprising a continuous contact with the touchscreen; the ultrasound scanner to switch from the SD-mode to the 2D-mode, in response to detecting a beginning of the continuous contact; the touchscreen to unfreeze the frozen 2D-mode ultrasound image, in response to the switch; the touchscreen to detect, during the continuous contact, a characteristic of the continuous contact; and the touchscreen to adjust the gate displayed on the unfrozen 2D-mode ultrasound image in accordance with the characteristic.

In some embodiments, the computer readable instructions, when executed by the processor, cause: the touchscreen to detect a termination of the continuous contact; the ultrasound scanner to switch, in response to the termination, from the 2D-mode to the SD-mode, in which the ultrasound scanner obtains a SD-mode ultrasound signal corresponding to the adjusted gate; and the touchscreen to adjust, in response to the termination, the display to: refreeze the 2D-mode ultrasound image; and display a live SD-mode ultrasound spectrum that corresponds to the adjusted gate.

The invention claimed is:

1. A method for switching an ultrasound scanner between a spectral Doppler mode ("SD-mode") and a two-dimensional (2D) ultrasound imaging mode ("2D-mode") comprising:
displaying, on a touchscreen that is communicatively connected to the ultrasound scanner, while the ultrasound scanner is operating in the SD-mode, a display comprising:
a frozen 2D-mode ultrasound image;
a gate that corresponds to the SD-mode, the gate superimposed on the frozen 2D-mode ultrasound image; and
a live SD-mode ultrasound spectrum that corresponds to the gate;
receiving an input comprising a single continuous contact with the touchscreen which single continuous contact:
switches, by a processor, in response to detecting a beginning of the single continuous contact, the ultrasound scanner from the SD-mode to the 2D-mode;
adjusts, by the processor in response to the switching, the display to unfreeze the frozen 2D-mode ultrasound image;
detects, by the processor, during the single continuous contact, a characteristic of the continuous contact; and
adjusts, by the processor, the gate displayed on the unfrozen 2D-mode ultrasound image in accordance with the characteristic.

2. The method of claim 1 comprising:
detecting, by the processor, a termination of the single continuous contact;
switching, in response to the termination, the ultrasound scanner from the 2D-mode to the SD-mode, in which the ultrasound scanner obtains an SD-mode ultrasound signal corresponding to the adjusted gate; and
adjusting the display, in response to the termination, to:
refreeze the 2D-mode ultrasound image; and
display a live SD-mode ultrasound spectrum that corresponds to the adjusted gate.

3. The method of claim 2, comprising:
displaying, on the touchscreen, an unfreeze button;
detecting a contact with the unfreeze button;
switching, by the processor, in response to detecting the contact, the ultrasound scanner from the SD-mode to the 2D-mode for a predetermined duration of time;
adjusting, by the processor, the display to unfreeze the frozen 2D-mode ultrasound image for the predetermined duration of time; and
switching, by the processor, the ultrasound scanner from the 2D-mode to the SD-mode after the predetermined duration of time.

4. The method of claim 3, wherein the predetermined duration of time is longer than a duration of the contact.

5. The method of claim 1, wherein the characteristic of the single continuous contact with the touchscreen comprises a drag gesture, and a position of the displayed gate is continuously updated during the drag gesture to track a displacement of the drag gesture.

6. The method of claim 1, wherein the characteristic of the single continuous contact with the touchscreen comprises a drag gesture, and an angular orientation of the displayed gate is continuously updated during the drag gesture in proportion to a displacement of the drag gesture.

7. The method of claim 1, wherein the characteristic of the single continuous contact with the touchscreen comprises a drag gesture, and a size of the displayed gate is continuously updated during the drag gesture in proportion to a displacement of the drag gesture.

8. The method of claim 1, wherein the single continuous contact with the touchscreen comprises two contact points and the characteristic of the single continuous contact is a drag gesture of the two contact points, and a position of the displayed gate is continuously updated during the drag gesture to track a displacement of the two contact points.

9. The method of claim 1, wherein the single continuous contact with the touchscreen comprises two contact points and the characteristic of the single continuous contact is a rotation gesture, and an angular orientation of the displayed gate is continuously updated during the rotation gesture in proportion to an angle of rotation of the rotation gesture.

10. The method of claim 1, wherein the single continuous contact with the touchscreen comprises two contact points and the characteristic of the single continuous contact is a spread or pinch gesture, and a size of the displayed gate is continuously updated during the spread or pinch gesture in proportion to a change in separation of the two contact points.

11. The method of claim 1, wherein the input begins on the frozen 2D-mode ultrasound image and continues on the unfrozen 2D-mode ultrasound image.

12. The method of claim 11, wherein the input is not on the displayed gate.

13. The method of claim 1, wherein the gate is adjusted more coarsely when the beginning of the single continuous contact is at a first location on the touchscreen than when the beginning of the single continuous contact is at a second location on the touchscreen.

14. The method of claim 1, wherein the SD-mode comprises a pulsed-wave Doppler mode.

15. The method of claim 1, wherein the 2D-mode comprises one of: B-mode, a combined B-mode/Color Doppler mode, or a combined B-mode/Power Doppler mode.

16. An ultrasound system that switches between a spectral Doppler mode ("SD-mode") and a two-dimensional (2D) ultrasound imaging mode ("2D-mode") comprising:
 an ultrasound scanner;
 a touchscreen;
 a processor that is communicatively connected to the ultrasound scanner and operatively connected to the touchscreen;
 non-transitory computer readable memory storing computer readable instructions, which, when executed by the processor cause:
  the touchscreen to display, while the ultrasound scanner is operating in the SD-mode:
   a frozen 2D-mode ultrasound image;
   a gate that corresponds to the SD-mode, the gate superimposed on the frozen 2D-mode ultrasound image; and
   a live SD-mode ultrasound spectrum that corresponds to the gate;
  the touchscreen to receive an input comprising a single continuous contact with the touchscreen, which single continuous contact causes:
   the ultrasound scanner to switch from the SD-mode to the 2D-mode, in response to detecting a beginning of the single continuous contact;
   the touchscreen to unfreeze the frozen 2D-mode ultrasound image, in response to the switch;
   the touchscreen to detect, during the single continuous contact, a characteristic of the single continuous contact; and
   the touchscreen to adjust the gate displayed on the unfrozen 2D-mode ultrasound image in accordance with the characteristic.

17. The system of claim 16 wherein the computer readable instructions, when executed by the processor, cause:
 the touchscreen to detect a termination of the single continuous contact;
 the ultrasound scanner to switch, in response to the termination, from the 2D-mode to the SD-mode, in which the ultrasound scanner obtains a SD-mode ultrasound signal corresponding to the adjusted gate; and
 the touchscreen to adjust, in response to the termination, the display to:
  refreeze the 2D-mode ultrasound image; and
  display a live SD-mode ultrasound spectrum that corresponds to the adjusted gate.

18. The system of claim 16 wherein the characteristic of the single continuous contact with the touchscreen comprises:
 a first drag gesture, wherein a position of the displayed gate is continuously updated during the first drag gesture to track a displacement of the first drag gesture;
 a second drag gesture, wherein an angular orientation of the displayed gate is continuously updated during the second drag gesture in proportion to a displacement of the second drag gesture;
 a third drag gesture, wherein a size of the displayed gate is continuously updated during the third drag gesture in proportion to a displacement of the third drag gesture;
 two first contact points, wherein the characteristic of the single continuous contact is a fourth drag gesture of the two first contact points, and the position of the displayed gate is continuously updated during the fourth drag gesture to track a displacement of the two first contact points;
 two second contact points, wherein the characteristic of the single continuous contact is a rotation gesture, and the angular orientation of the displayed gate is continuously updated during the rotation gesture in proportion to an angle of rotation of the rotation gesture; or
 two third contact points, wherein the characteristic of the single continuous contact is a spread or pinch gesture, and a size of the displayed gate is continuously updated during the spread or pinch gesture in proportion to a change in separation of the two third contact points.

19. A portable computing device that switches an ultrasound scanner between a spectral Doppler mode ("SD-mode") and a two-dimensional (2D) ultrasound imaging mode ("2D-mode") comprising:
 a touchscreen;
 a processor that is communicatively connected to the ultrasound scanner and operatively connected to the touchscreen;
 non-transitory computer readable memory storing computer readable instructions, which, when executed by the processor cause:
  the touchscreen to display, while the ultrasound scanner is operating in the SD-mode:
   a frozen 2D-mode ultrasound image;
   a gate that corresponds to the SD-mode, the gate superimposed on the frozen 2D-mode ultrasound image; and
   a live SD-mode ultrasound spectrum that corresponds to the gate;
  the touchscreen to receive an input comprising a single continuous contact with the touchscreen, wherein the single continuous contact causes:
   the ultrasound scanner to switch from the SD-mode to the 2D-mode, in response to detecting a beginning of the single continuous contact;
   the touchscreen to unfreeze the frozen 2D-mode ultrasound image, in response to the switch;
   the touchscreen to detect, during the single continuous contact, a characteristic of the single continuous contact; and
   the touchscreen to adjust the gate displayed on the unfrozen 2D-mode ultrasound image in accordance with the characteristic.

20. The portable computing device of claim 19 wherein the computer readable instructions, when executed by the processor, cause:
 the touchscreen to detect a termination of the single continuous contact;
 the ultrasound scanner to switch, in response to the termination, from the 2D-mode to the SD-mode, in which the ultrasound scanner obtains a SD-mode ultrasound signal corresponding to the adjusted gate; and
 the touchscreen to adjust, in response to the termination, the display to:
  refreeze the 2D-mode ultrasound image; and
  display a live SD-mode ultrasound spectrum that corresponds to the adjusted gate.

* * * * *